(12) United States Patent
McKay

(10) Patent No.: US 7,833,270 B2
(45) Date of Patent: *Nov. 16, 2010

(54) IMPLANT DEPOTS TO DELIVER GROWTH FACTORS TO TREAT OSTEOPOROTIC BONE

(75) Inventor: William F. McKay, Memphis, TN (US)

(73) Assignee: Warsaw Orthopedic, Inc

( * ) Notice: Subject to any disclaimer, the term of this patent is extended or adjusted under 35 U.S.C. 154(b) by 251 days.

This patent is subject to a terminal disclaimer.

(21) Appl. No.: 11/418,947

(22) Filed: May 5, 2006

(65) Prior Publication Data

US 2007/0259019 A1 Nov. 8, 2007

(51) Int. Cl.
  *A61F 2/44* (2006.01)
  *A61K 38/16* (2006.01)
  *A61K 38/00* (2006.01)

(52) U.S. Cl. ............ 623/16.11; 623/17.11; 424/198.1; 514/2

(58) Field of Classification Search ........................ None
See application file for complete search history.

(56) References Cited

U.S. PATENT DOCUMENTS

| 5,344,654 | A | * | 9/1994 | Rueger et al. ............... 424/423 |
| 5,972,384 | A | * | 10/1999 | Thut et al. .................... 424/484 |
| 5,972,385 | A | * | 10/1999 | Liu et al. ..................... 424/486 |
| 6,004,573 | A | * | 12/1999 | Rathi et al. .................. 424/426 |
| 6,274,159 | B1 | | 8/2001 | Marotta et al. |
| 6,346,123 | B1 | | 2/2002 | McKay |
| 6,371,988 | B1 | | 4/2002 | Pafford et al. |
| 6,375,935 | B1 | * | 4/2002 | Constantz .................... 424/57 |
| 6,613,091 | B1 | | 9/2003 | Zdeblick et al. |
| 2004/0167637 | A1 | * | 8/2004 | Biscup ..................... 623/23.75 |
| 2005/0084542 | A1 | * | 4/2005 | Rosenberg et al. .......... 424/549 |
| 2005/0152949 | A1 | | 7/2005 | Hotchkiss et al. |

* cited by examiner

*Primary Examiner*—Elizabeth C. Kemmerer
*Assistant Examiner*—Xiaozhen Xie

(57) ABSTRACT

The present invention relates to the design and composition of a depot implant for optimal delivery of growth factors to treat osteoporotic bone, in that such depot implant is constructed to be in a cylinder (rod) or sphere shape and have a natural or synthetic polymer scaffold with or without impregnated calcium phosphate particles. The density of the depot is higher than a typical BMP sponge carrier to facilitate it's implantation and slower release of the growth factor. The scaffold is such that it has adequate porosity and pore size to facilitate growth factor seeding and diffusion throughout the whole of the bone structure resulting in increased bone mineral density in the osteoporotic bone. In addition, the shape of the depot implant allows for delivery through a cannula or large bore needle.

8 Claims, 4 Drawing Sheets

IMPLANT DEPOTS TO DELIVER GROWTH FACTORS TO TREAT OSTEOPOROTIC BONE

FIELD OF THE INVENTION

The present invention relates to the design and composition of an implant that is used as a growth factor depot to treat osteoporotic bone. More particularly, the depot is in the shape of a small cylinder (straight or curved) or sphere that can be delivered into osteoporotic bone through a cannula or large bore needle.

BACKGROUND OF THE INVENTION

Osteoporosis is a major public health threat for an estimated 44 million Americans, or 55 percent of the people 50 years of age and older. In the United States, 10 million individuals are estimated to already have the disease and almost 34 million more are estimated to have low bone mass, placing them at increased risk for osteoporosis. Osteoporosis is often called a "silent disease" because bone loss occurs without symptoms. Indeed, people may not know that they have osteoporosis until their bones become so weak that a sudden strain, bump or fall causes a fracture or a vertebra to collapse.

Osteoporosis, or porous bone, is a disease characterized by low bone mass and structural deterioration of bone tissue, leading to bone fragility and an increased susceptibility to fractures, especially of the hip, spine and wrist, although any bone can be affected. If not prevented or if left untreated, osteoporosis can progress painlessly until a bone breaks. These broken bones, also known as fractures, occur typically in the hip, spine, and wrist. It is estimated that Osteoporosis is responsible for more than 1.5 million fractures annually, including: over 300,000 hip fractures; and approximately 700,000 vertebral fractures; 250,000 wrist fractures; and 300,000 fractures at other sites.

While osteoporosis is often thought of as an older person's disease, it can strike at any age. One in two women and one in four men over age 50 will have an osteoporosis-related fracture in her/his remaining lifetime. Any bone can be affected, but of special concern are fractures of the hip and spine. A hip fracture almost always requires hospitalization and major surgery. It can impair a person's ability to walk unassisted and may cause prolonged or permanent disability or even death. Spinal or vertebral fractures also have serious consequences, including loss of height, severe back pain, and deformity.

Depending upon the condition of the patient, new bone ingrowth is accomplished by one or more mechanisms such as osteogenesis, osteoconduction and osteoinduction. It can be appreciated that the needs of a child are different from an aging patient afflicted with osteoporosis. Accordingly, there is no "one size fits all" approach towards optimizing the healing conditions in a patient.

Current treatments of osteoporotic disease, such as a vertebral body known as a vertebroplasty, utilize cements that set-up in vivo after injection, however, these treatments have attendant risks. These cements have the potential to extrude into the spinal canal causing neural compression or to be forced into the venous blood network leading to emboli.

In addition, the following medications are approved by the FDA for postmenopausal women to prevent and/or treat osteoporosis:
  Bisphosphonates:
    Alendronate and alendronate plus vitamin D (brand name Fosamax® and Fosamax® plus D). Alendronate is approved as a treatment for osteoporosis in men and is approved for treatment of glucocorticoid (steroid)-induced osteoporosis in men and women.
    Ibandronate (brand name Boniva®).
    Risedronate and risedronate with calcium (brand name Actonel® and Actonel® with Calcium). Risedronate is approved for prevention and treatment of glucocorticoid-induced osteoporosis in men and women.
  Calcitonin (brand name Miacalcin®).
  Estrogen/Hormone Therapy:
    Estrogens (brand names, such as Climara®, Estrace®, Estraderm®, Estratab®, Ogen®, Ortho-Est®, Premarin®, Vivelle® and others).
    Estrogens and Progestins (brand names, such as Activella™, FemHrt®, Premphase®, Prempro® and others).
  Parathyroid Hormone—Teriparatide (PTH (1-34) (brand name Fortéo®). Parathyroid hormone is approved for the treatment of osteoporosis in men who are at high risk of fracture.
  Selective Estrogen Receptor Modulators (SERMs):
  Raloxifene (brand name Evista®).

Treatments under investigation include sodium fluoride, vitamin D metabolites, and other bisphosphonates and selective estrogen receptor modulators. These therapies, however, only result in approximately a 0-3% increase in bone mineral density (BMD) per year. On the other hand, local delivery of a growth factor via depot implant results in a 10-50% BMD increase within a few months.

Despite the advances recently made in the art, there is an immediate need for improved medical devices, methods and systems for treating osteoporotic bone.

SUMMARY OF THE INVENTION

The present invention fills the foregoing need by providing a growth factor depot implant and system for facilitating implantation of the depot into a host bone comprising implanting an implant depot loaded with a growth factor. Local delivery of a growth factor will result in 10-50% increase in bone mineral density within a few months.

In accordance with a first aspect of the present invention, a growth factor depot implant design provides a physical feature to facilitate implantation and retention of the implant in the desired anatomical location for optimal clinical efficiency in treating osteoporotic disease.

In an embodiment of the invention, the depot implant is in the shape of a small cylinder (straight or curved rod) or sphere that can be delivered into osteoporotic bone through a cannula or large bore needle. In a preferred embodiment, the depot would be about 1 to about 5 mm in diameter and about 5 to about 20 mm in length.

In another embodiment of the invention, provision is made for the depot implant to have a composition comprising a dense collagen scaffold impregnated with calcium phosphate particles. In yet another embodiment of the invention, the scaffold is designed with a central hollow cavity that can be filled with a growth factor. In a preferred embodiment such growth factor is then slowly released through the porous depot walls.

Another aspect of the invention provides for application of the growth factor to the depot during fabrication of the depot. A preferred embodiment of the invention, provides for a method of applying the growth factor to the depot at the time of surgery comprising dripping on or soaking in a solution of growth factor and, optionally further, can be placed into the internal structure of the dense depot by placing the depot into a vacuum chamber intra-operatively. Yet further, the growth factor can be injected into the depot.

Advantages of the design and composition of the implant depot are such that a slow release of the growth factor can be maintained thus avoiding transient bone resorption near the implant due to the high dose of growth factor in the depot. Another advantage to the design and composition of the implant depot is the prevention of entrance of the growth factor into venous system.

These and other objects and advantages of the present invention will be apparent from the descriptions herein.

DEFINITIONS

Figure 1:
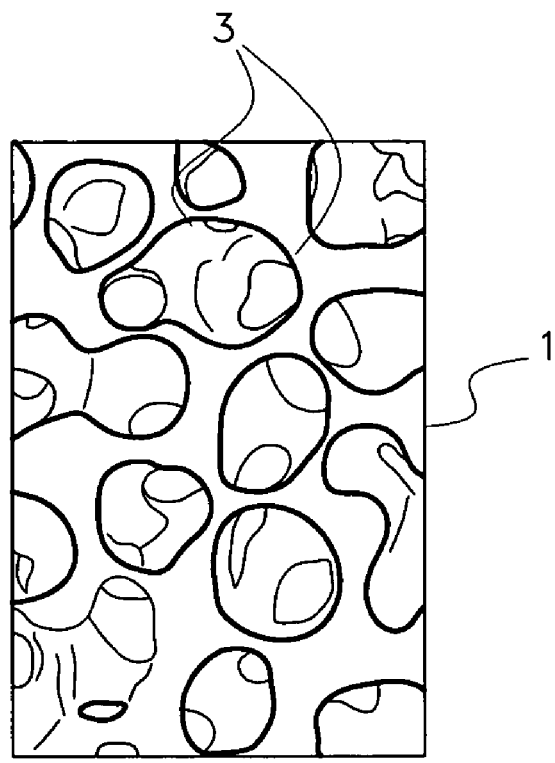
FIG. 1 depicts bone density in a healthy bone versus an osteoporotic bone.
Figure 1:
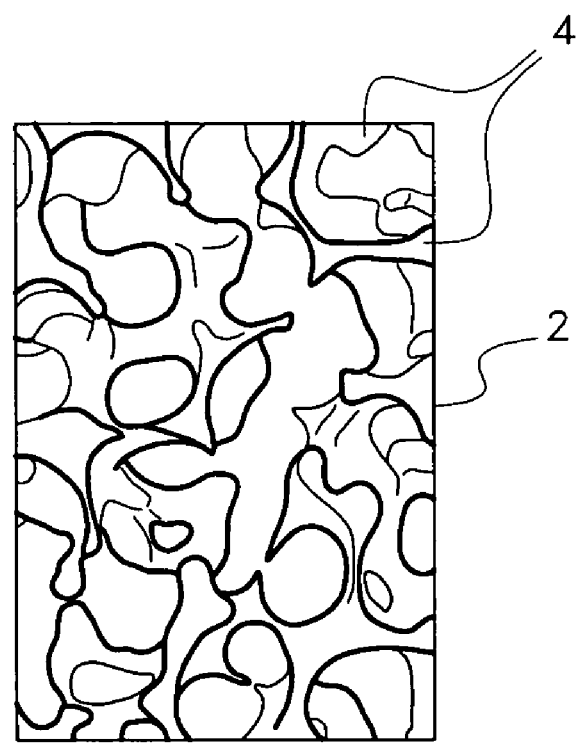

To aid in the understanding of the invention, the following non-limiting definitions are provided:

The term "osteoconduction" refers to the ability to stimulate the attachment, migration, and distribution of vascular and osteogenic cells within the graft material. The physical characteristics that affect the graft's osteoconductive activity include porosity, pore size, and three-dimensional architecture. In addition, direct biochemical interactions between matrix proteins and cell surface receptors play a major role in the host's response to the graft material.

The term "osteogenic" refers to the ability of a graft material to produce bone independently. To have direct osteogenic activity, the graft must contain cellular components that directly induce bone formation. For example, a collagen matrix seeded with activated MSCs would have the potential to induce bone formation directly, without recruitment and activation of host MSC populations. Because many osteoconductive scaffolds also have the ability to bind and deliver bioactive molecules, their osteoinductive potential will be greatly enhanced.

The term "osteoinduction" refers to the ability to stimulate the proliferation and differentiation of pluripotent mesenchymal stem cells (MSCs). In endochondral bone formation, stem cells differentiate into chondroblasts and chondrocytes, laying down a cartilaginous ECM, which subsequently calcifies and is remodeled into lamellar bone. In intramembranous bone formation, the stem cells differentiate directly into osteoblasts, which form bone through direct mechanisms. Osteoinduction can be stimulated by osteogenic growth factors, although some ECM proteins can also drive progenitor cells toward the osteogenic phenotype.

The term "patient" refers to a biological system to which a treatment can be administered. A biological system can include, for example, an individual cell, a set of cells (e.g., a cell culture), an organ, or a tissue. Additionally, the term "patient" can refer to animals, including, without limitation, humans.

The term "treating" or "treatment" of a disease refers to executing a protocol, which may include administering one or more drugs to a patient (human or otherwise), in an effort to alleviate signs or symptoms of the disease. Alleviation can occur prior to signs or symptoms of the disease appearing, as well as after their appearance. Thus, "treating" or "treatment" includes "preventing" or "prevention" of disease. In addition, "treating" or "treatment" does not require complete alleviation of signs or symptoms, does not require a cure, and specifically includes protocols which have only a marginal effect on the patient.

DETAILED DESCRIPTION

For the purposes of promoting an understanding of the principles of the invention, reference will now be made to preferred embodiments and specific language will be used to describe the same. It will nevertheless be understood that no limitation of the scope of the invention is thereby intended, and that alterations and further modifications of the invention and such further applications of the principles of the invention as herein being contemplated would normally occur to one skilled in the art to which the invention relates.

Referring now to the figures, FIG. 1 illustrates a microscopic picture regional view of the condition of normal bone 1 versus that of osteoporotic bone 2. Bone normally has an internal mesh-like structure, the density of which may vary at different points. However, osteoporosis causes the bone mineral density to be reduced, such that the bone micro-architecture is disrupted and the amount and variety of non-collagenous proteins in bone is changed. In other words and as can be seen from such view, the porousness of the spacing 3 of the bone tissue in a normal bone 3 is much denser than that of the porousness of the spacing 4 of the bone tissue in an osteoporotic bone 2. Such increase in spacing account for increasing brittleness and weakening of the bone and allows for implantation of the growth factor depot in the spacing.

In the practice of the invention the growth factors include but are not limited to bone morphogenic proteins, for example, BMP-2, rhBMP-2, BMP-4, rhBMP-4, BMP-6, rhBMP-6, BMP-7 [OP-1], rhBMP-7, GDF-5, and rhGDF-5, as disclosed, for example, in the U.S. Pat. Nos. 4,877,864; 5,013,649; 5,661,007; 5,688,678; 6,177,406; 6,432,919; 6,534,268; and 6,858,431, and in Wozney, J. M., et al. (1988) *Science,* 242(4885):1528-1534. Bone morphogenic proteins have been shown to be excellent at growing bone and there are several products being tested. Extensive animal testing has already been undertaken, and human trials are finished and in process for these products. rhBMP-2 delivered on an absorbable collagen sponge (INFUSE® Bone Graft, Medtronic Sofamor Danek, Memphis, Tenn.) has been used inside titanium fusion cages and resulted in fusion in 11 out of 11 patients in a pilot study and 99% of over 250 patients in a pivotal study. In July, 2002 INFUSE® Bone Graft received FDA approval for use in certain types of spine fusion. A pilot study with BMP-2 delivered on a ceramic carrier was recently published and reported a 100% successful posterolateral fusion rate. BMP-7 (OP-1) has reported 50-70% successful posterolateral lumbar fusion results in human studies to date. On May 4, 2004, INFUSE® Bone Graft was approved for acute, open fractures of the tibial shaft (Bosse et al. *NEJM*

347(24): 1924-1931, 2002; Govender et al. *JBJS* 84(12): 2123-2134, 2002). Studies with these and other BMP's are underway. However, it is important to note that use of BMP's may add cost to an already very expensive operation.

Additionally, suitable growth factors include, without limitation, LIM mineralization protein, platelet derived growth factor (PDGF), transforming growth factor β (TGF-β), insulin-related growth factor-I (IGF-I), insulin-related growth factor-II (IGF-II), fibroblast growth factor (FGF), and beta-2-microglobulin (BDGF II), as disclosed in the U.S. Pat. No. 6,630,153, and PTH, PGE2-aganonist, and statins.

Figure 2:
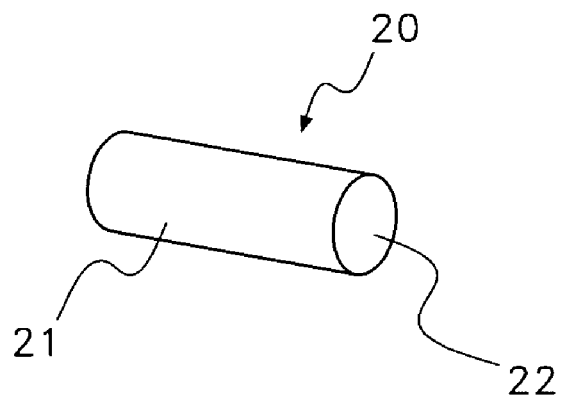
FIG. 2 depicts a perspective view of one embodiment of a growth factor depot implant.

Referring now to FIG. 2, an example of growth factor depot implant 20 is illustrated. The depot implant 20 can either be in the shape of a small cylinder (straight or curved rod) or sphere, and in construction may be either cannulated or solid. The surface of the depot implant may be either smooth, threaded, or any combination thereof. Herein, the cylinder or rod shape is intended to indicate any shape with a longitudinal axis longer along one direction than in other directions. As shown in the longitudinal direction, the depot implant 20 is constructed such that it is usually 5 to 20 mm in length and such that its surface can be either a smooth or convoluted surface 21. The cross-sectional shape across the longitudinal axis may be any shape, but is preferably elliptical or circular. In addition, the depot implant may be either straight or curved in such longitudinal direction. As shown in vertical direction, the depot implant 20 is constructed such that it is 1 to 5 mm in diameter and such that its end surface 22 can be shaped such that it is either flat, rounded, or convoluted in shape.

Figure 6:
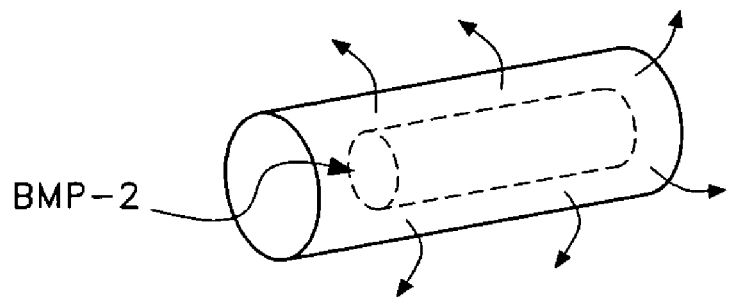
FIG. 6 depicts a perspective view of another embodiment of a growth factor depot implant.

Referring now to FIG. 6, another example of growth factor depot implant is illustrated. In this embodiment, depot implant is cylindrical in shape, but is constructed such that it has a hollow interior chamber (shown by the dotted line). The chamber may itself follow the exterior cylindrical shape or may be of any shape, in so long as the exterior structure is not compromised. In a preferred embodiment, the chamber is filled with a growth factor which then diffuses out of as indicated by the arrows. In addition, or alternatively, the depot implant could contain a radiopaque marker consisting of barium, calcium, or such other suitable material. Such marker can be utilized for tracking purposes and ensuring proper positioning through a radiograph.

As such, the depot implant can be strategically inserted into osteoporotic bone areas in a minimally invasive procedure by entering the body through the skin or through a body cavity or anatomical opening, thus allowing for the smallest damage possible to these structures and correspondingly resulting in less operative trauma for the patient. Preferably, the depot implant is placed in an area of least bone marrow density for maximum impact of the growth factor.

The growth factor depot may be constructed from a number of materials consisting of natural and synthetic polymers, in solid or gel form, or a combination of each. Examples of plastic materials that the rods could be fabricated from are polyorthoesters (POE), Polylacticglycolic acid (PLGA) Polysacharides (Saber technology), Polycapralactone, Polyfumarate, Tyrosine polycarbonate, etc. Examples of materials that the gel could be fabricated from are Polyethylene glycol (PEG), Polysacharides (Saber technology), Polyorthoesters, Hyaluronic acid, Chitosan, Alginate, Albumin, etc.

Figure 3:
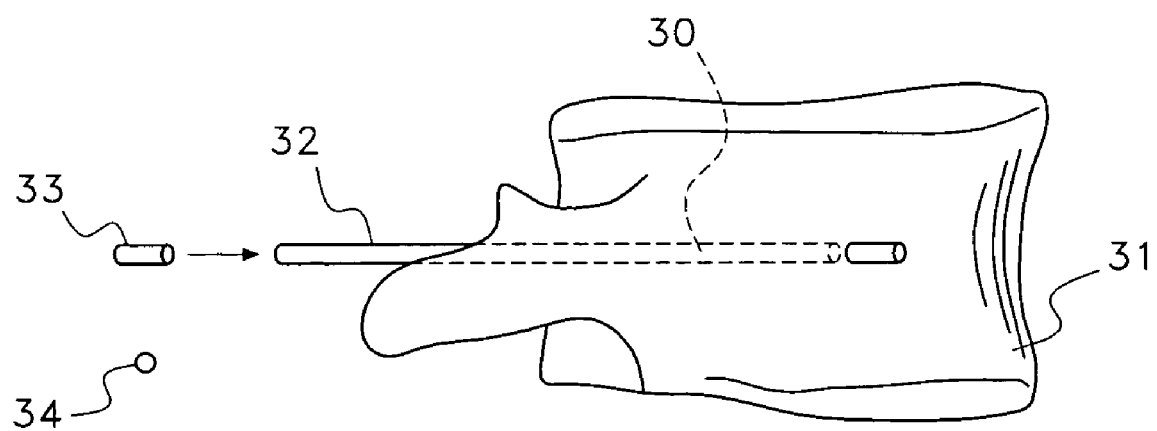
FIG. 3 depicts a perspective view of an embodiment of the insertion of a growth factor depot implant into a vertebral body of the spine.
Figure 7:
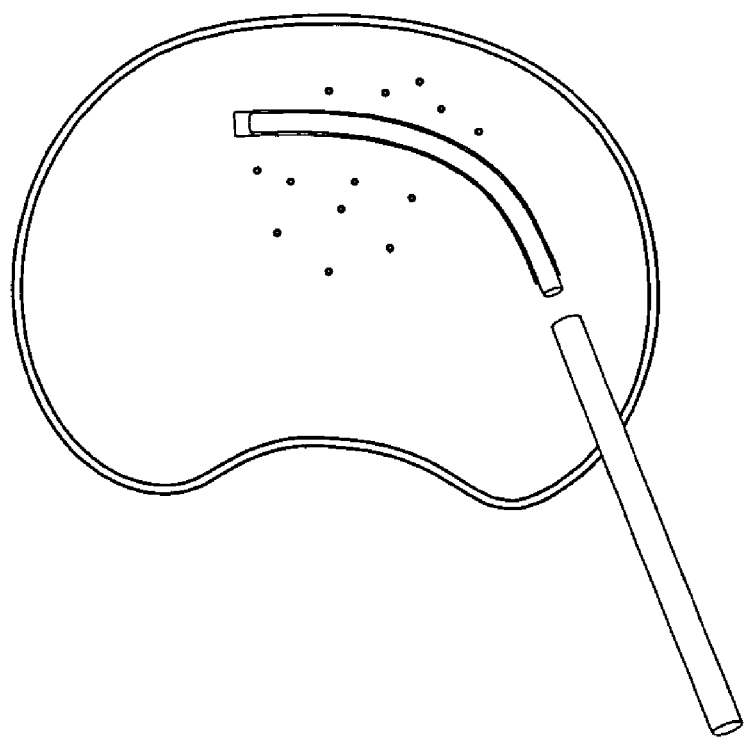
FIG. 7 depicts a top view of an embodiment of the insertion of a growth factor depot implant into a vertebral body of the spine.

Referring now to FIGS. 3 and 7, alternatively either a cylinder (straight or curved rod) or sphere shaped BMP-loaded depot implants and cannula for insertion into a vertebral body is illustrated. In the first step, (illustrated in FIG. 3) a bore hole 30 is drilled by a cannula 32 into a vertebral body 31. In an embodiment, such access to the space is gained by a trocar (a sharp pointed needle (not shown)) attached to the cannula 32, allowing for puncture of the body to get into the intended space in the bone. In another embodiment, such access to the space is gained by an orthopedic tool as is well know in the art. Alternatively, or in addition, to the first step, a K-wire, with fluoroscopic imaging, may be used to identify a desired location of the depot implant and then drilling with a canulated drill may be done. In a second step, alternatively either a straight-rod shaped depot implant 33, a sphere-shaped depot implant 34 or a curved rod shaped depot implant (shown in FIG. 7) is then inserted into the vertebral body 31 through the cannula 32. Selection of the type of depot may be based upon a number of factors, including: the shape and/or size of the bone into which the depot is to be implanted; the percentage of bone density (i.e., the porousness of the remaining bone); and/or the desired speed and distribution of diffusion of the growth factor into the bone; a combination of such factors, etc. Accordingly, as is shown in FIG. 7, a curved depot implant is utilized to match the shape of the vertebral body and thus allow for a more uniform distribution of the growth factor.

Application of the growth (osteoinductive) factor to the depot may occur at the time of surgery or in any other suitable manner. For example, such application may comprise of dripping or soaking the depot implant in a solution of growth factor. Alternatively (or additionally), the growth factor may be further placed into the internal structure of the depot by placing the depot into a vacuum chamber intra-operatively. Further alternatively (or additionally), the growth factor may be further placed into the internal structure of the depot via insertion of a needle into the center of the depot. It is to be understood, of course, that the internal construction of the depot implant, either solid or hollow, would be independent of the method by which the growth factor may be introduced to the depot implant but may play a role in selection of such method. In many cases, the growth factor may be applied to either the calcium phosphate material or the binding matrix (i.e., collagen) prior to combining the materials and forming into the final depot shape. Indeed, the growth factor can be blended into the natural or synthetic polymer (i.e., POE) and poured into molds of the final shape of the depot implant. Alternatively, the factor, such as a bone morphogenetic protein in a suitable liquid carrier, may be applied onto and/or into the porous load depot body after forming into the final shape by soaking, dripping, etc.

It should be noted, of course, that the BMP load in the depot acts as an osteoinductive factor. Indeed, the preferred osteoinductive factors are the recombinant human bone morphogenetic proteins (rhBMPs) because they are available in unlimited supply and do not transmit infectious diseases. Most preferably, the bone morphogenetic protein is a rhBMP-2, rhBMP-4, rhBMP-7, or heterodimers thereof.

Recombinant BMP-2 can be used at a concentration of about 0.4 mg/ml to about 10.0 mg/ml, preferably near 1.5 mg/ml. However, any bone morphogenetic protein is contemplated including bone morphogenetic proteins designated as BMP-1 through BMP-18. BMPs are available from Wyeth, Cambridge, Mass. and the BMPs and genes encoding them may also be prepared by one skilled in the art as described in U.S. Pat. No. 5,187,076 to Wozney et al.; U.S. Pat. No. 5,366, 875 to Wozney et al.; U.S. Pat. No. 4,877,864 to Wang et al.; U.S. Pat. No. 5,108,922 to Wang et al.; U.S. Pat. No. 5,116, 738 to Wang et al.; U.S. Pat. No. 5,013,649 to Wang et al.; U.S. Pat. No. 5,106,748 to Wozney et al.; and PCT Patent Nos. WO93/00432 to Wozney et al.; WO94/26893 to Celeste et al.; and WO94/26892 to Celeste et al. All osteoinductive factors are contemplated whether obtained as above or isolated from bone. Methods for isolating bone morphogenetic protein from bone are described, for example, in U.S. Pat. No. 4,294,753 to Urist and Urist et al., 81 PNAS 371, 1984.

Figure 4:
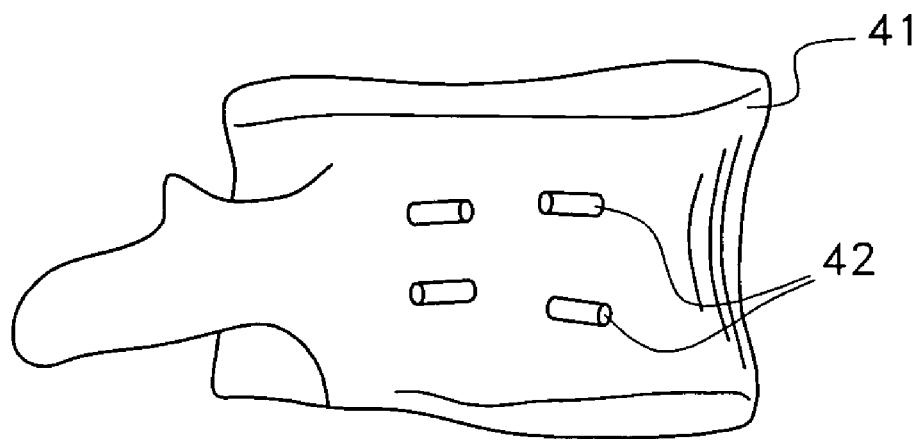
FIG. 4 depicts a perspective view of an embodiment of several growth factor depots in the implanted stage in a vertebral body of the spine.
Figure 5:
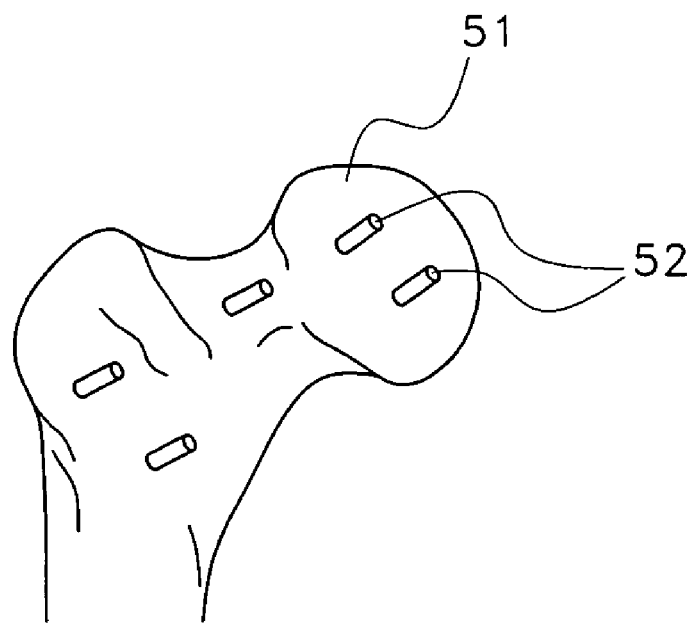
FIG. 5 depicts a perspective view of an embodiment of several growth factor depots in an implanted stage in a femur body of the hip.

Referring now to FIGS. 4 and 5, a vertebral body 41 of the spine and a femur body 51 of the hip are shown implanted with several growth factor depot implants 42 and 52, respectively. The depot implants composition may be comprised of a dense collagen scaffold impregnated with calcium phosphate particles. The scaffold as disclosed herein has a high porosity and an adequate pore size in order to facilitate growth factor seeding and diffusion throughout the whole of the bone structure. Preferably, the scaffold is constructed to be in a range of 2-40% porosity. In addition, the scaffold is biodegradable such that it is absorbed by the surrounding bone tissues without the necessity of a surgical removal. The rate at which degradation occurs is designed to coincide with the optimal release of the growth factor. Furthermore, according to an embodiment of the present invention, a collagen material is used to make up the scaffold as it is tough and inextensible, with great tensile strength, the main component of cartilage, ligaments and tendons, and the main protein component of bone and connective tissue. As mentioned above, selection of the shape and size of the depot implant may be done on the basis of a number of factors.

The dense collagen scaffold is impregnated with calcium phosphate particles. As calcium phosphate is a minerals containing calcium ions (Ca2+) together with orthophosphates (PO43−), metaphosphates or pyrophosphates (P2O74−) and occasionally hydrogen or hydroxide ions, it is easily absorbed by the body as a raw material for new bone cell growth. In a preferred embodiment of the invention, the calcium phosphate is either hydroxyapaptite or tri-calcium phosphate, or a biphasic blend of the two, ideally in a ratio of 15HA/85TCP to 35HA/65TCP.

Accordingly, in this aspect of the invention the density of the depot is much higher than a typical BMP sponge carrier so that the release of the BMP is much slower. As such, the longer release kinetic properties of this depot avoids the potential for local transient bone resorption, and instead a more rapid increase in bone deposition, which therefore ultimately achieves a higher bone mineral density with osteoporotic bone. In addition, the calcium phosphate component of the depot will also facilitate the prevention of local bone resorption by providing slower release of the BMP due to its increased binding potential and also act as a local source of calcium and phosphate to the cells attempting to deposit new bone.

In some embodiments, the osteogenic compositions used in this invention further comprise a therapeutically effective amount to stimulate or induce bone growth of a substantially pure bone inductive or growth factor or protein in a pharmaceutically acceptable carrier. The choice of carrier material for the osteogenic composition is based on biocompatibility, biodegradability, mechanical properties and interface properties as well as the structure of the load bearing member. The particular application of the compositions of the invention will define the appropriate formulation. Potential carriers include calcium phosphates, collagen, hyaluronic acid, polyorthoesters, polylactic acids, poly glycoloic acids, PLGA copolymers, polyanhydrides, polymeric acrylic esters, calcium sulphates and demineralized bone. The carrier may be any suitable carrier capable of delivering the proteins, nucleotide sequences, or the like. Most preferably, the carrier is capable of being eventually resorbed into the body. One preferred carrier is an absorbable collagen sponge marketed by Integra LifeSciences Corporation under the trade name Helistat® Absorbable Collagen Hemostatic Agent. Another preferred carrier is a biphasic calcium phosphate ceramic. Ceramic blocks and granules are commercially available from Sofamor Danek Group, Deggendorf, Germany.

All publications cited in the specification, both patent publications and non-patent publications, are indicative of the level of skill of those skilled in the art to which this invention pertains. All these publications are herein fully incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

What is claimed:

1. A depot implant comprising:
a physical structure which is shaped and allows for implantation and retention into a host bone; and a dense polymer scaffold making up the construct of the physical structure, the dense polymer scaffold impregnated with calcium phosphate particles comprising hydroxyapatite (HA) and tricalcium phosphate (TCP) in a ratio of 15 HA: 85 TCP to 35 HA: 65 TCP and comprising collagen and no polysaccharide, and a growth factor loaded in the dense polymer scaffold for delivery to the host bone and the dense polymer scaffold is disposed throughout the entire implant, and has a central hollow chamber disposed throughout the implant to facilitate seeding and diffusion of the growth factor and the implant has a porosity of 2% to 40%.

2. The depot implant according to claim 1, wherein the physical structure is generally in the shape of one of a cylinder and a sphere.

3. The depot implant according to claim 2, wherein the cylinder shape is either straight or curved.

4. The depot implant according to claim 2, wherein the cylinder shape is 5 to 20 mm in length.

5. The depot implant according to claim 1, wherein the depot implant is generally in the shape of a cylinder shape and is 1 to 5 mm in diameter.

6. The depot implant according to claim 1, wherein the physical structure is conducive to delivery to the host bone through one of a cannula or large bore needle.

7. The depot implant according to claim 1, wherein the growth factor is at least one of: BMP-2, rhBMP-2, BMP-4, rhBMP-4, BMP-6, rhBMP-6, BMP-7 (OP-1), rhBMP-7, GDF-5, rhGDF-5, LIM mineralization protein, platelet-derived growth factor (PDGF), transforming growth factor β (TGF-β), insulin-related growth factor-I (IGF-I), insulin-related growth factor-II (IGF-II), fibroblast growth factor (FGF), beta-2-microglobulin (BDGF II), PTH, and PGE2 agonist.

8. The depot implant according to claim 1, wherein the growth factor is loaded into the dense polymer scaffold by means of at least one of a step of: dripping a solution of growth factor onto the depot implant; soaking the depot implant in a solution of growth factor; and placing the depot implant and growth factor into a vacuum chamber.

* * * * *

UNITED STATES PATENT AND TRADEMARK OFFICE
CERTIFICATE OF CORRECTION

PATENT NO. : 7,833,270 B2
APPLICATION NO. : 11/418947
DATED : November 16, 2010
INVENTOR(S) : McKay Page 1 of 1

It is certified that error appears in the above-identified patent and that said Letters Patent is hereby corrected as shown below:

On the Cover Page, item (73), under "Assignee", in Column 1, Line 1, delete "Inc" and insert -- Inc. (U.S.) --, therefor.

Signed and Sealed this
Fifteenth Day of March, 2011

David J. Kappos
*Director of the United States Patent and Trademark Office*